(12) United States Patent
Sako

(10) Patent No.: US 6,859,513 B2
(45) Date of Patent: Feb. 22, 2005

(54) RADIOGRAPHIC APPARATUS AND METHOD, AND CONTROL APPARATUS AND METHOD UPON RADIOGRAPHY

(75) Inventor: Tsukasa Sako, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 389 days.

(21) Appl. No.: 10/026,976

(22) Filed: Dec. 27, 2001

(65) Prior Publication Data

US 2002/0080918 A1 Jun. 27, 2002

(30) Foreign Application Priority Data

Dec. 27, 2000 (JP) .................................. 2000-399332

(51) Int. Cl.⁷ .............................................. G01N 23/00
(52) U.S. Cl. ................................ 378/16; 378/901; 378/8
(58) Field of Search ................................ 378/16, 98.2, 8, 378/901, 62, 4, 115, 116, 151

(56) References Cited

U.S. PATENT DOCUMENTS

| 4,458,267 | A | * | 7/1984 | Dolazza ..................... 378/98.7 |
| 5,357,554 | A | * | 10/1994 | Schneiderman et al. .... 378/155 |
| 5,368,033 | A | | 11/1994 | Moshfeghi ............... 128/653.4 |
| 5,471,987 | A | | 12/1995 | Nakazawa et al. .......... 128/659 |
| 5,644,611 | A | | 7/1997 | McShane et al. ............. 378/98 |
| 5,655,084 | A | * | 8/1997 | Pinsky et al. .................. 705/3 |
| 5,740,267 | A | * | 4/1998 | Echerer et al. ............. 382/132 |
| 5,748,509 | A | * | 5/1998 | Fewster ......................... 703/6 |
| 5,991,457 | A | | 11/1999 | Ito et al. ..................... 382/254 |
| 6,084,939 | A | | 7/2000 | Tamura ..................... 378/98.2 |
| 6,178,225 | B1 | * | 1/2001 | Zur et al. .................. 378/98.2 |
| 6,259,767 | B1 | * | 7/2001 | Neumann et al. .......... 378/151 |
| 6,289,115 | B1 | * | 9/2001 | Takeo ........................ 382/130 |
| 6,422,749 | B1 | * | 7/2002 | Polkus et al. ............... 378/205 |
| 6,501,827 | B1 | * | 12/2002 | Takasawa ................... 378/116 |
| 6,504,897 | B1 | * | 1/2003 | Yonekawa ..................... 378/63 |
| 6,614,873 | B1 | * | 9/2003 | Taylor et al. ................. 378/62 |
| 6,644,851 | B1 | * | 11/2003 | Kumagai .................... 378/167 |
| 6,707,880 | B2 | * | 3/2004 | Yamayoshi ................... 378/92 |

FOREIGN PATENT DOCUMENTS

| JP | 55-12429 | 1/1980 |
| JP | 56-11395 | 2/1981 |
| JP | 9-98970 | 4/1997 |

* cited by examiner

Primary Examiner—David V. Bruce
Assistant Examiner—Irakli Kiknadze
(74) Attorney, Agent, or Firm—Fitzpatrick, Cella, Harper & Scinto

(57) ABSTRACT

A radiographic apparatus for obtaining an X-ray image on the basis of examination request information received from an externa ol apparatus, determines a radiographing condition by giving the received examination request information preference to a default radiographing condition corresponding to the received examination request information.

38 Claims, 18 Drawing Sheets

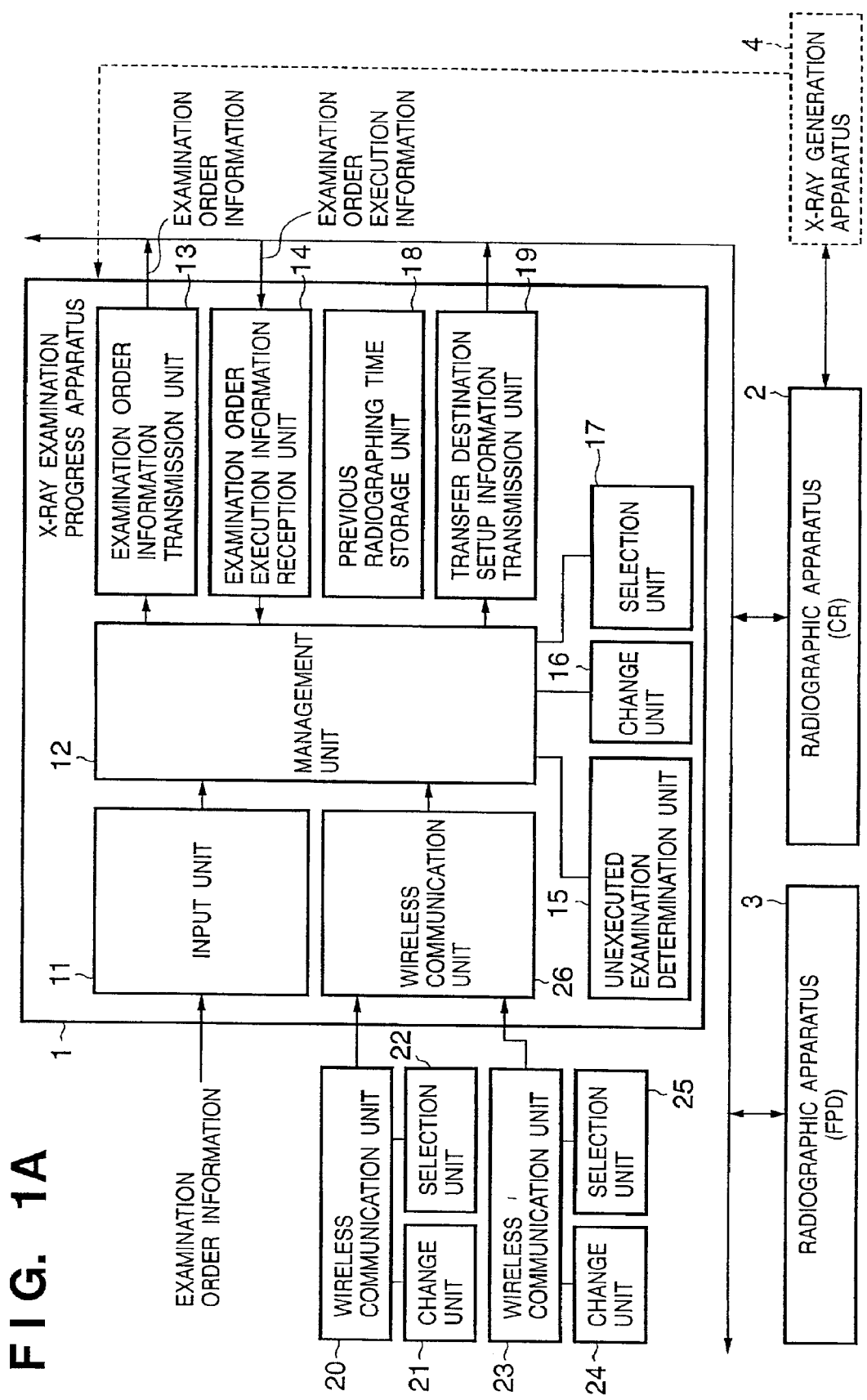

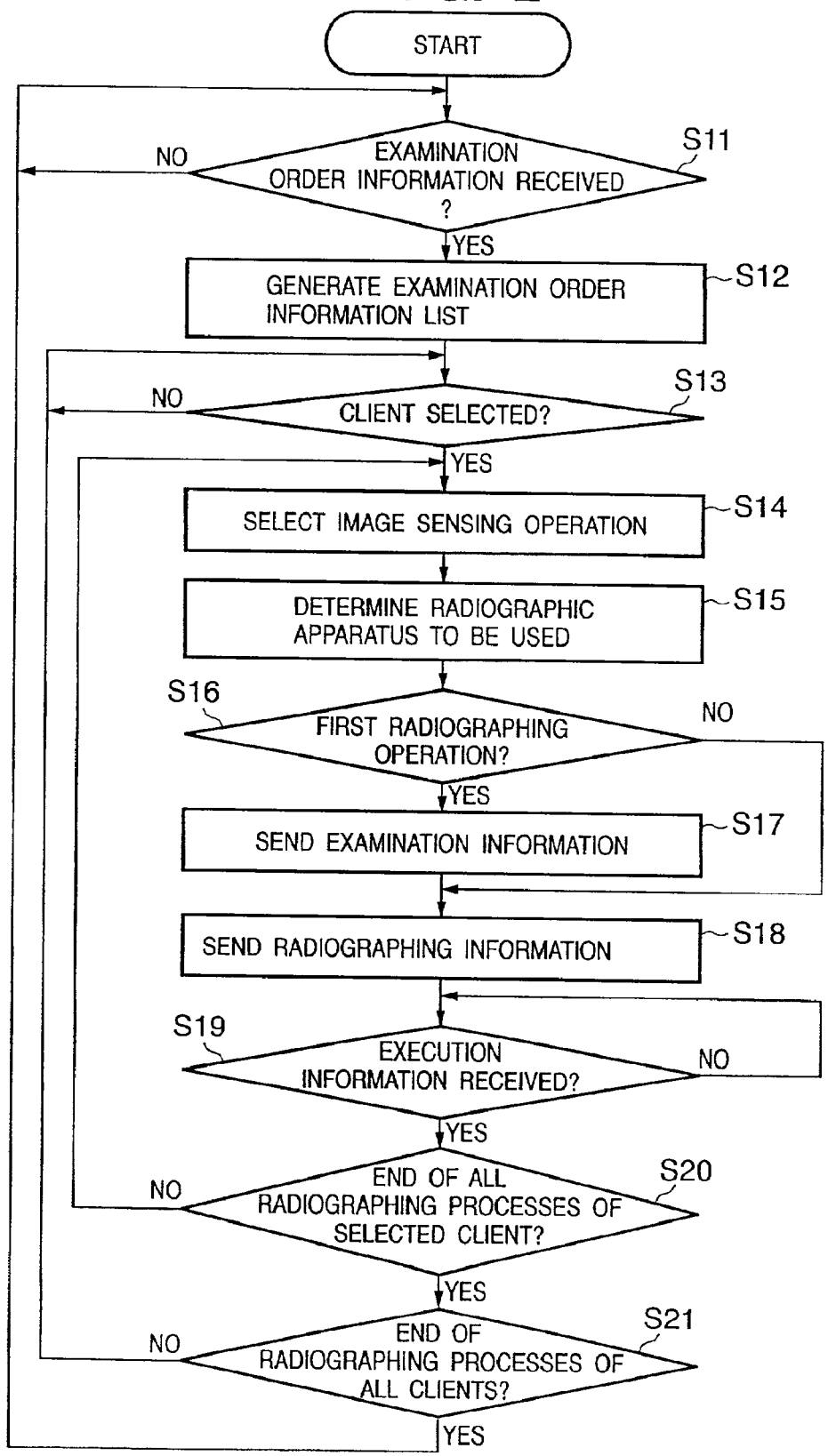

FIG. 3

| ITEM | |
|---|---|
| EXAMINATION STATE | UNEXAMINED |
| RECEPTION NO. | 123-4567 |
| ID | 1-23-456 |
| NAME | Tokkyo, Taro |
| DATE OF BIRTH | APRIL 16, 1965 |
| GENDER | MALE |
| WEIGHT | 80kg |
| HEIGHT | 180cm |
| PREGNANCY | NO |
| INFECTION | NO |
| TRANSFER DESTINATION OF IMAGE | SERVER 1, PRINTER 2 |
| EXECUTION INFORMATION RETURN DESTINATION | PROGRESS APPARATUS 1 |
| DICOM TAG DATA DESCRIPTION INFORMATION* | (0010, 1000) = A |
| RADIOGRAPHING COUNT | 2 |

FIG. 4

| ITEM | RADIOGRAPHING OPERATION 1 | RADIOGRAPHING OPERATION 2 |
|---|---|---|
| RADIOGRAPHING OPERATION STATE | UNEXECUTED | UNEXECUTED |
| RADIOGRAPHING METHOD NAME | CHEST FRONT | CHEST SIDE |
| RADIOGRAPHING METHOD ID (RADIOGRAPHING PORTION INFORMATION) | 1000 | 1000 |
| RADIOGRAPHING DIRECTION | PA | LR |
| RIGHT/LEFT | NONE | NONE |
| TUBE VOLTAGE | 120kV | 100kV |
| TUBE CURRENT | (NO VALUE AVAILABLE) | 100mA |
| EXPOSURE TIME | (NO VALUE AVAILABLE) | 30msec |
| HEIGHT OFFSET VALUE | +20mm | |
| X-RAY APERTURE VALUE | 35cm × 35cm | |
| OUTPUT FORMAT | 14 × 17" SIZE | |
| DICOM TAG DATA DESCRIPTION INFORMATION* | (0010, 1000) = B | |
| CHARACTER SIZE, POSITION | LARGE, LOWER CENTRAL | |

FIG. 6

| RADIOGRAPHING METHOD NAME | RADIOGRAPHING METHOD ID | DIRECTION | RADIOGRAPHIC APPARATUS |
|---|---|---|---|
| CHEST FRONT | 1000 | PA | FPD |
| CHEST SIDE | 1000 | LR | FPD |
| KNEE | 2000 | AP | FPD |
| KNEE | 2000 | LR | FPD |
| KNEE | 2000 | SKYLINE | CR |
| KNEE | 2000 | PA | CR |
| ...... | ...... | ...... | ...... |
| ...... | ...... | ...... | ...... |

FIG. 8

| ITEM | ORDER PARAMETER | RADIOGRAPHING PARAMETER SET |
|---|---|---|
| EXAMINATION INFORMATION | | |
| EXAMINATION STATE | UNEXAMINED | (N/A) |
| RECEPTION NO. | 123-4567 | (N/A) |
| ID | 1-23-456 | (N/A) |
| NAME | Tokkyo, taro | (N/A) |
| DATE OF BIRTH | APRIL 16, 1965 | (N/A) |
| GENDER | MALE | (N/A) |
| WEIGHT | 80kg | (N/A) |
| HEIGHT | 180cm | (N/A) |
| PREGNANCY | NO | (N/A) |
| INFECTION | NO | (N/A) |
| TRANSFER DESTINATION OF IMAGE | SERVER 1, PRINTER 2 | SERVER 1, PRINTER 2 |
| EXECUTION INFORMATION RETURN DESTINATION | PROGRESS APPARATUS 1 | (N/A) |
| RADIOGRAPHING COUNT | 2 | (N/A) |
| RADIOGRAPHING INFORMATION | | |
| RADIOGRAPHING OPERATION STATE | UNEXECUTED | (N/A) |
| RADIOGRAPHING METHOD NAME | CHEST FRONT | CHEST FRONT |
| RADIOGRAPHING METHOD ID (IMAGE SENSING PORTION INFORMATION) | 1000 | 1000 |
| RADIOGRAPHING DIRECTION | PA | PA |
| RIGHT/LEFT OF ORGAN | NONE | (N/A) |
| RADIOGRAPHIC APPARATUS | FPD | (N/A) |
| TUBE VOLTAGE | 120kV | 120kV |
| TUBE CURRENT | (NO VALUE AVAILABLE) | 100mA |
| EXPOSURE TIME | (NO VALUE AVAILABLE) | USE STATISTICAL INFORMATION |
| DENSITY SETUP OF GENERATION APPARATUS | +2 | 0 |
| GRAYSCALE PROCESSING | (NO VALUE AVAILABLE) | (NO VALUE AVAILABLE) |
| HEIGHT OFFSET VALUE | +20mm | +20mm |
| X-RAY APERTURE VALUE | 35cm × 35cm(*) | 35cm × 35cm(*) |
| OUTPUT FORMAT | 14 × 17" SIZE | 14 × 17" SIZE |
| IMAGE HORIZONTAL REVERSE | (N/A) | REVERSE |
| DICOM TAG DATA DESCRIPTION INFORMATION | (NO VALUE AVAILABLE) | (0010, 1000) = B |
| CHARACTER SIZE, POSITION | LARGE, LOWER CENTRAL | LARGE, LOWER CENTRAL |

FIG. 9

| ITEM | BASIC PARAMETER SET | SYSTEM SETUP |
|---|---|---|
| TRANSFER DESTINATION OF IMAGE | SERVER 1, PRINTER 2 | SERVER 1 |
| RADIOGRAPHING METHOD NAME | CHEST FRONT | (N/A) |
| RADIOGRAPHING METHOD ID (RADIOGRAPHING PORTION INFORMATION) | 10000 | (N/A) |
| RADIOGRAPHING DIRECTION | PA | (N/A) |
| TUBE VOLTAGE | 100kV | (N/A) |
| TUBE CURRENT | 100mA | (N/A) |
| EXPOSURE TIME | USE STATISTICAL INFORMATION | (N/A) |
| DENSITY SETUP OF GENERATION APPARATUS | 0 | 0 |
| GRAYSCALE PROCESSING | (NO VALUE AVAILABLE) | FOLLOW DENSITY SETUP IF AVAILABLE |
| HEIGHT OFFSET VALUE | +0mm | +0mm |
| X-RAY APERTURE VALUE | 35cm × 35cm | 35cm × 43cm |
| OUTPUT FORMAT | LARGE SQUARE | 14 × 17" SIZE |
| IMAGE HORIZONTAL REVERSE | FOLLOW CHEST TABLE | FOLLOW CHARACTER OUTPUT TABLE |
| DICOM TAG DATA DESCRIPTION INFORMATION | USE SYSTEM VALUE | (0010, 1000) = B |
| CHARACTER SIZE, POSITION | LARGE, LOWER CENTRAL | FOLLOW CHARACTER OUTPUT TABLE |

FIG. 10

| AGE | X-RAY APERTURE VALUE |
|---|---|
| 15 OR OLDER | USE DESIGNATED APERTURE |
| UNDER 15 | USE APERTURE VALUE 20% SMALLER THAN DESIGNATED APERTURE |

FIG. 11

| RADIOGRAPHING DIRECTION | HORIZONTAL REVERSE |
|---|---|
| PA | REVERSE |
| AP | NOT REVERSE |
| LR | NOT REVERSE |
| RL | NOT REVERSE |

FIG. 12

| RADIOGRAPHING DIRECTION | RIGHT/ LEFT OF ORGAN | HORIZONTAL REVERSE | CHARACTER SIZE/ POSITION |
|---|---|---|---|
| PA | LEFT | NOT REVERSE | LARGE, LOWER LEFT |
| AP | LEFT | REVERSE | LARGE, LOWER RIGHT |
| PA | RIGHT | NOT REVERSE | LARGE, LOWER RIGHT |
| AP | RIGHT | REVERSE | LARGE, LOWER LEFT |

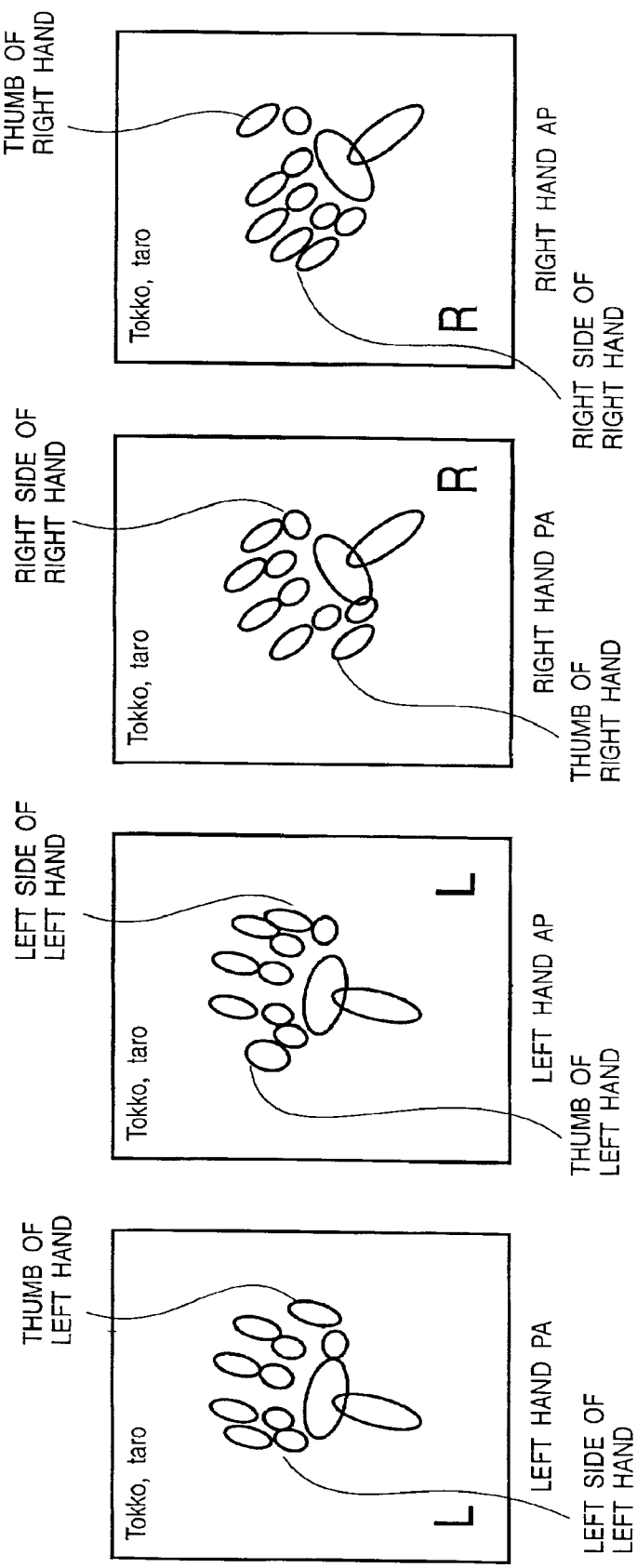

RADIOGRAPHIC APPARATUS AND METHOD, AND CONTROL APPARATUS AND METHOD UPON RADIOGRAPHY

FIELD OF THE INVENTION

The present invention relates to a radiographic apparatus and method, and a control apparatus and method upon radiography.

BACKGROUND OF THE INVENTION

Conventionally, when image diagnosis is made in the medical field, a film image sensed using X-rays is observed while being set on a schaukasten. However, since a normal X-ray film is set to emphasize contrast within the density range from 1.0D to 1.5D that allows easy observation in quest of easy observation of a portion to be diagnosed, if the image sensing condition slightly deviates from an appropriate condition, an image suffers overexposure or underexposure, thus adversely influencing diagnosis based on image reading.

With the advance of computers in recent years, computerization has infiltrated into the medical field. This trend is also rapid in the image diagnostic field, and various CT apparatuses, ultrasonic wave diagnostic apparatuses, diagnostic apparatuses using radioisotope, and the like have prevailed remarkably. A concept called "total image diagnosis" that totally diagnoses various modality images by connecting various diagnostic apparatuses via a computer has been entertained. However, an X-ray film image is essentially an analog image. Hence, although the X-ray film image is most frequently used in image diagnosis and is considered very important, it cannot satisfactorily merge into total image diagnosis, and disturbs computerization of the image diagnosis field.

In recent years, an X-ray image sensing (radiographic) apparatus using a solid-state image sensing element has been developed, and a radiographic apparatus suitable for the aforementioned computerization is beginning to be used for X-ray images (radiographs). When this radiographic apparatus is used, the already radiographed image can undergo contrast adjustment, and since a radiographed image can be obtained in real time, if radiographing operation fails, a re-radiographing operation can be done immediately.

When this apparatus is used, a radiographed image is immediately displayed, and images ordered in a hospital can be efficiently radiographed. Hence, the time required per examination can be relatively shorter than other diagnostic apparatuses such as CT apparatuses, ultrasonic wave diagnostic apparatuses, diagnostic apparatuses using radioisotope, and the like. However, if pre-processes such as input of a patient's name, patient ID, and the like are complicated and time-consuming upon examination, the examination time is prolonged consequently, resulting in poor radiographing efficiency.

In a conventional radiographing operation, X-ray generation conditions suitable for radiographing are manually input to an X-ray generation apparatus while checking an ordered examination sheet. However, when a radiographic apparatus is introduced, the operator must input setups such as radiographing conditions and the like to the X-ray generation apparatus and radiographic apparatus, and must execute image setup processes such as reverse, rotation, and the like of each radiographed image, resulting in poor radiographing efficiency.

To solve this problem, an X-ray examination (radiographing) progress system that links an X-ray examination progress apparatus and a radiographic apparatus is prevalently used. Since the X-ray examination progress system receives order information from an ordering apparatus in a hospital, patient information and radiographing information are correctly sent from the X-ray examination progress apparatus to the radiographic apparatus via this link, and the need for pre-processes such as input of a patient's name, patient ID, and the like, and input and selection of a portion to be radiographed can be obviated.

In a hospital, a doctor often combines a plurality of radiographing operations in one order. Therefore, the ordering apparatus handles orders for each examination. For example, in "chest abdomen examination", one package of three radiographing operations, i.e., chest front radiographing operation, chest side radiographing operation, and abdomen front radiographing operation is called one examination. Ordered examination information is converted into digital data together with patient information such as a patient ID, patient's name, the presence/absence of pregnancy, and the like, of a patient to be examined, and is sent to the X-ray examination progress apparatus in a radiographing room. Such order information for each examination will be referred to as examination order information hereinafter, and each of one or more pieces of radiographing information contained in the examination order information will be referred to as radiographing order information hereinafter.

However, in some cases, the setups of radiographing operations and acquisition processes of the radiographic apparatus are to be done on the radiographic apparatus side on the basis of the transferred examination order information. Such case will be explained below.

For example, in order to set a minimum required X-ray dose on a patient as well as to satisfactorily print a portion to be radiographed on a film, X-ray aperture value, relative position (an offset value of the X-ray tube central position with respect to the image sensor central position), such as a relative height of an X-ray tube and an image sensor, and X-ray generation condition such as a tube voltage are controlled before a radiographing operation is performed on the basis of information such as an age, weight, height, gender, and the like in the examination order information. Furthermore, after a radiographing operation is performed, control of extracting a radiographed image must be done in accordance with output format information such as division amount of an output image (number of images within an output image), portrait, landscape, and the like, so that an irradiation field portion of a radiograph corresponding to the X-ray aperture appropriately is within a film.

FIGS. 14A and 14B show examples of chest radiographing. In a chest front AP radiographing (radiographing in which X-rays pass through the chest from the abdomen side to the back side) shown in FIG. 14A, a radiographed image can be output as it is. However, in a chest front PA radiographing (radiographing in which X-rays pass through the chest from the back side to the abdomen side) shown in FIG. 14B, a radiographed image must be reversed horizontally upon display. Upon reading an image, a doctor normally observes a film with patient's heart on the right side. For this reason, control such as rotation, reverse, and the like of an image in a direction designated in advance is required in correspondence with a radiographing direction such as AP, PA, or the like of radiographing order information. However, such horizontal reverse is made in accordance with AP/PA only when a specific portion such as a chest is to be radiographed. Upon radiographing other portions such as a head or the like, such process is inhibited.

FIGS. 15A and 15B show examples when a patient's name is superimposed on a radiographed image. When characters are superimposed on an output image, it is a common practice to superimpose the patient's name at the lower central position in a chest front radiographing, as shown in FIG. 15A, and at the upper left position in a chest side radiographing, as shown in FIG. 15B. This is because when a portion to be radiographed is formed on nearly the entire surface of the film, a region which is clinically not important is generally the lower central region in a chest front radiographing, and the upper left region in chest side radiographing. For this reason, a setup process for rendering characters in accordance with character output position information of the radiographing order information is required.

FIGS. 16A to 16D show more complicated examples of the process printing characters on a radiographed image.

When X-rays strike from the back side of the hand upon radiographing the left hand, letter "L" that means the left hand is laid out on the left side (small finger side) of the hand when viewed from the back of the hand, i.e., on the left side of the image, as shown in FIG. 16A. When X-rays strike from the palm side of the left hand, letter "L" that means the left hand is laid out on the left side (small finger side) of the hand when viewed from the back of the hand, i.e., on the right side of the image, as shown in FIG. 16B. Likewise, when X-rays strike from the back side of the hand upon radiographing the right hand, letter "R" that means the right hand is laid out on the right side (small finger side) of the hand when viewed from the back of the hand, i.e., on the right side of the image, as shown in FIG. 16C. When X-rays strike from the palm side of the right hand, letter "R" that means the right hand is laid out on the right side (small finger side) of the hand when viewed from the back of the hand, i.e., on the left side of the image, as shown in FIG. 16D. In this manner, a setup process for rendering characters in accordance with portion information, radiographing direction, right/left information (right-and-left distinction of an organ or portion such as the right and left hands) of the radiographing order information is required.

If a long exposure time is set upon determining the grid moving speed, grid must be moved slowly; if a short exposure time is set, grid must be moved quickly. For example, if the grid stands still without being moved, interference occurs between sensor sampling and the grid, and moiré is generated on the image. If the grid moves slowly even when a short exposure time is set, moiré is generated as in a case wherein the grid stands still. For this reason, a setup process for setting the grid moving speed based on the setup exposure time is required.

Furthermore, when a printer or image storage device as an image transfer destination breaks down and is switched to a backup printer or backup image storage device upon determining image transfer information, the image transfer destination must be designated again in accordance with the examination order information. In this case, if many radiographic apparatuses are used, setups must be changed in those apparatuses, resulting in much extra labor. Since the printer or image storage device may break down unexpectedly, a setup change process of the transfer destinations is required not only for order information, radiographing of which is not started yet, but also for examination, radiographing of which is underway, examination, radiographing of which is complete but information of which is not transferred yet, and examination which is suspended due to a transfer error.

The ordering system preferably integrally manages examination ID values generated by respective radiographic apparatuses in terms of management in an image storage device as an image transfer destination. Such ID values are often important for a matching process if the ordering system of a facility is linked with an image storage system of the facility. However, such values differ depending on facilities, and information provided by the ordering system must be recorded on a header of an image file in a specific description manner upon image transfer.

In all the above examples, examination order information that lacks a parameter of image sensing order information must be processed. More specifically, in some facilities, for example, right/left information may not be sent, and no information of a predetermined parameter may be sent in case of emergency, or information of a predetermined parameter may not be input due to input errors or the like. Furthermore, a setup exposure time may not be determined in advance in a case of radiographing using auto exposure control (AEC), and is not included in the examination order information.

SUMMARY OF THE INVENTION

The present invention has been made in consideration of the above situation, and has as its object to improve operability and radiographing efficiency by automatically making setups required for radiographing operations and processing of radiographs.

According to the present invention, the foregoing object is attained by providing a radiographic apparatus for obtaining an X-ray image on the basis of examination request information received from an external apparatus, comprising: a storage unit adapted to store at least one default radiographing condition; and a condition determination unit for determining a radiographing condition on the basis of the received examination request information and a default radiographing condition, stored in the storage unit, corresponding to the received examination request information, wherein the received examination request information is given preference to the default radiographing condition.

According to the present invention, the foregoing object is also attained by providing a control apparatus which is connectable to a plurality of radiographic apparatuses, and outputs information to the radiographic apparatuses on the basis of examination request information received from an external apparatus, comprising: an apparatus selection unit for selecting a radiographic apparatus to be used on the basis of the received examination request information; and a communication unit adapted to send information that pertains to the examination request information to the selected radiographic apparatus.

Further, the foregoing object is also attained by providing a control apparatus which is connectable to a radiographic apparatus, and outputs information to the radiographic apparatus on the basis of examination request information received from an external apparatus, comprising: a condition determination unit for determining a radiographing condition on the basis of the received examination request information; and a communication unit adapted to send the determined radiographing condition to the radiographic apparatus.

Furthermore, the foregoing object is also attained by providing a radiographing method for obtaining an X-ray image on the basis of examination request information received from an external apparatus, comprising: obtaining a default radiographing condition from a storage unit based on the received examination request information; and determining a radiographing condition on the basis of the received examination request information and the obtained default radiographing condition, wherein the received examination request information is given preference to the default radiographing condition.

Further, the foregoing object is also attained by providing a control method for outputting information to one of a plurality of radiographic apparatuses on the basis of examination request information received from an external apparatus, comprising: selecting a radiographic apparatus to be used on the basis of the received examination request information; and sending information that pertains to the examination request information to the selected radiographic apparatus.

Further, the foregoing object is also attained by providing a control method for outputting information to one of a plurality of radiographic apparatuses on the basis of examination request information received from an external apparatus, comprising: determining a radiographing condition on the basis of the received examination request information; and sending the determined radiographing condition to the radiographic apparatus.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

FIG. 1A is a block diagram mainly showing details of the arrangement of an X-ray examination progress apparatus in a digital radiographic system according to an embodiment of the present invention;

FIG. 2 is a flow chart showing the processing sequence of the X-ray examination progress apparatus according to the embodiment of the present invention;

FIG. 3 is a table showing an example of items and information values of examination information;

FIG. 4 is a table showing an example of items and information values of radiographing information;

FIG. 6 is a table showing an example of combinations of radiographing metod IDs, radiographing directions, and radiographic apparatuses;

FIG. 8 is a table showing an example of a determined parameter set and system information according to the embodiment of the present invention;

FIG. 9 is a table showing an example of a basic parameter set and system setup values;

FIG. 10 is a table for explaining a change process in the parameter set setup process according to the embodiment of the present invention;

FIG. 11 is a table for explaining a reverse process according to the embodiment of the present invention;

FIG. 12 is a table for explaining a reverse process (character size/position) according to the embodiment of the present invention;

FIGS. 16A to 16D are views showing another prior art in which the character is superimposed on a radiograph.

DETAILED DESCRIPTION OF THE PREFERRED EMBODIMENT

A preferred embodiment of the present invention will be described in detail in accordance with the accompanying drawings.

In this embodiment, a digital radiographing operation will be exemplified.

Figure 1B:
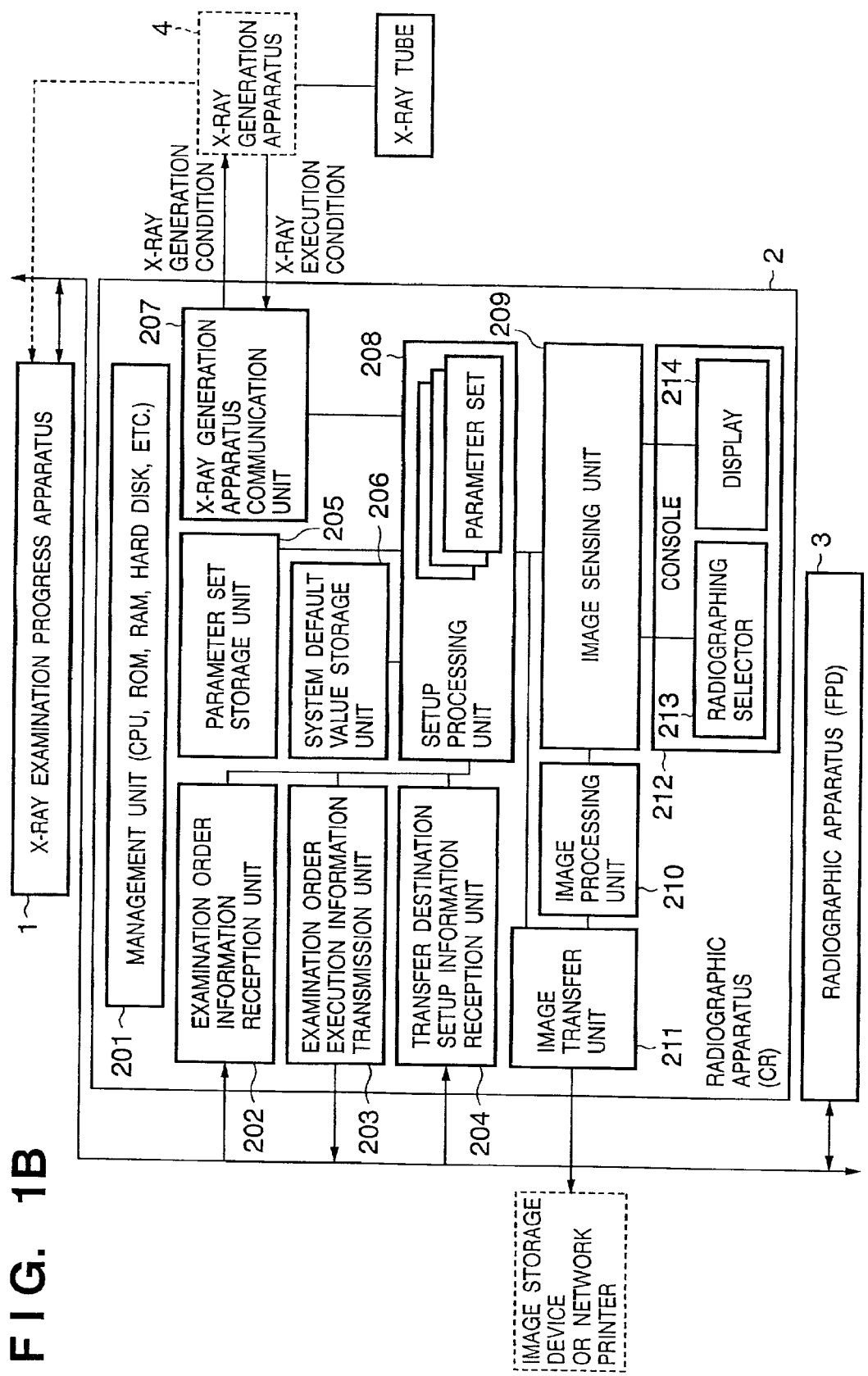
FIG. 1B is a block diagram mainly showing details of the arrangement of a radiographic apparatus (CR) in the digital radiographic system according to the embodiment of the present invention.
Figure 1C:
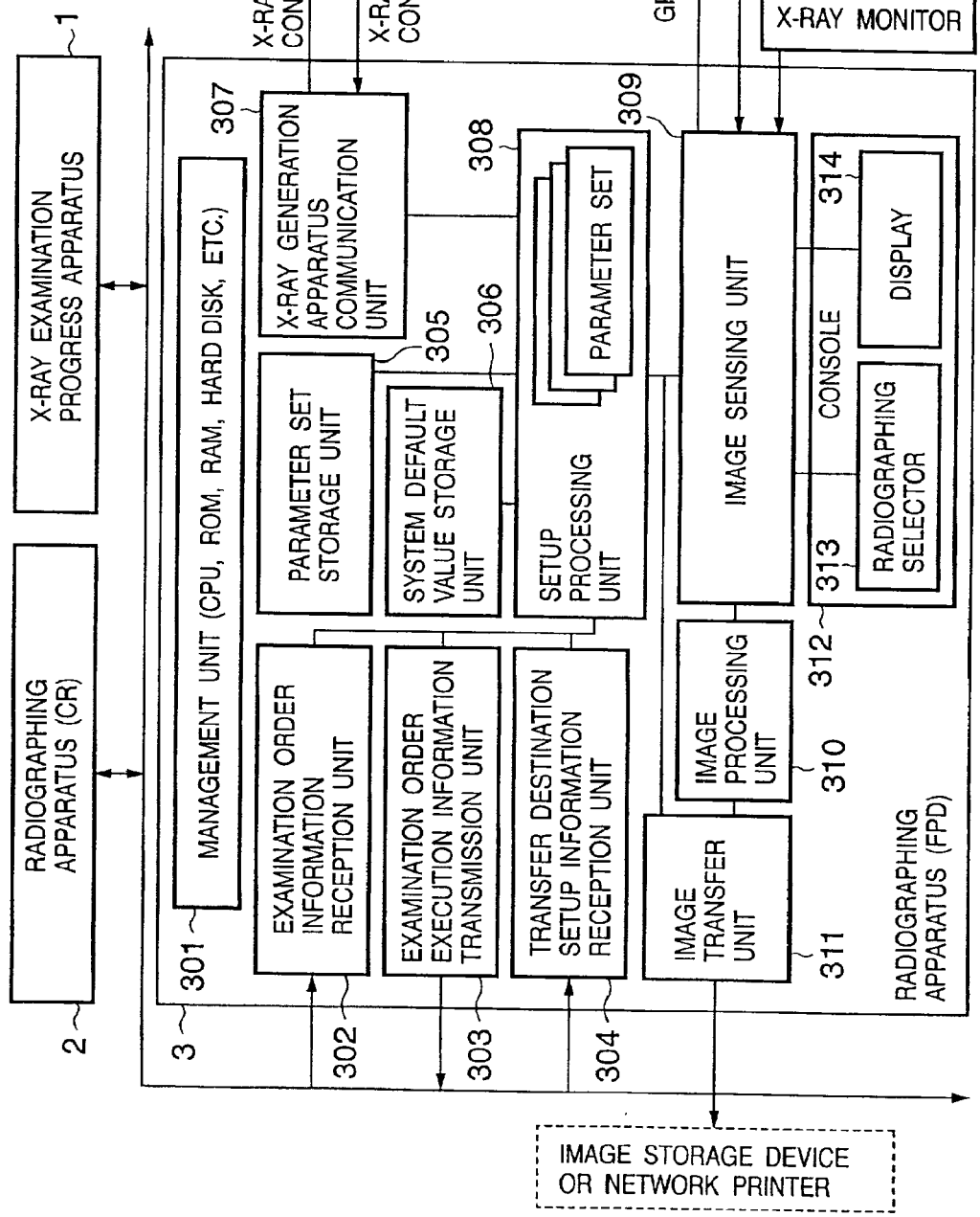
FIG. 1C is a block diagram mainly showing details of the arrangement of a radiographic apparatus (FPD) in the digital radiographic system according to the embodiment of the present invention.

FIGS. 1A to 1C are block diagrams showing the arrangement of a digital radiographic system in this embodiment. Referring to FIGS. 1A to 1C, reference numeral 1 denotes an X-ray examination (radiographing) progress apparatus; 2 and 3, digital radiographic apparatuses; and 4 and 5, X-ray generation apparatuses connected to the digital radiographic apparatuses 2 and 3, respectively.

In this embodiment, two digital radiographic apparatuses 2 and 3 are connected to one X-ray examination progress apparatus 1 for the sake of simplicity. However, one or three or more digital radiographic apparatuses may be connected.

In this embodiment, the digital radiographic apparatus 2 is a computed radiography apparatus that uses a sensor, which is called an imaging plate and reads X-ray image (radiograph) information stored in a fluorescent member of the imaging plate using a laser beam, and will be referred to as CR hereinafter. This CR is strong in a cassette radiographing operation. The digital radiographic apparatus 3 is an apparatus that uses a sensor unit having an upright bucky stand which includes a flat panel detector, comprising solid-state image sensing elements, for capturing an X-ray image, and will be referred to as FPD hereinafter.

The X-ray examination progress apparatus 1 comprises an input unit 11, management unit 12, examination order information transmission unit 13, examination order execution information reception unit 14, unexecuted examination determination unit 15, change unit 16, selection unit 17, previous radiographing time storage unit 18, and transfer destination setup information transmission unit 19. The CR 2 and FDP 3 respectively comprise management units 201 and 301, each of which includes a CPU, ROM, RAM, hard disk, and the like, examination order information reception units 202 and 302, examination order execution information transmission units 203 and 303, transfer destination setup information reception units 204 and 304, parameter set storage units 205 and 305, system default value storage units 206 and 306, X-ray generation apparatus communication units 207 and 307, setup processing units 208 and 308, image sensing units 209 and 309, image processing units 210 and 310, image transfer units 211 and 311, and consoles 212 and 312. The consoles 212 and 312 respectively comprise radiographing selectors 213 and 313, and displays 214 and 314.

The operation of the digital radiographic system with the above arrangement will be described in detail below with reference to FIGS. 2 to 12.

FIG. 2 is a flow chart showing the processing sequence of the X-ray examination progress apparatus 1. In step S11 in FIG. 2, the X-ray examination progress apparatus 1 waits for input of examination order information (examination request information). When a doctor places an on-line order of a required examination from an ordering apparatus (not shown), the examination order data (examination order information) is sent to the X-ray examination progress apparatus 1.

The examination order information contains examination information that includes patient information of each client, and at least one radiographing information to be used in a radiographing operation. FIG. 3 shows an example of items and information values of the examination information, and FIG. 4 shows an example of items and information values for radiographing operations of the radiographing information.

Figure 5:
FIG. 5 shows an example of an examination order information list according to the embodiment of the present invention.

If the X-ray examination progress apparatus 1 receives the examination order information via the input unit 11 (YES in step S11), the management unit 12 generates and displays an examination order information list shown in FIG. 5 in step S12. If the examination order information list has already been generated, that list is updated to reflect the new received examination order information.

The operator selects one client to be examined from the displayed examination order information list using the selection unit 17 (step S13). In this embodiment, the selection unit 17 selects a client to be examined from the displayed list using a mouse, keyboard, or the like (not shown) to set it in a selected state, and that selection is fixed by pressing an examination start button 21 using the mouse, keyboard, or the like in that state. Note that the X-ray examination progress apparatus 1 automatically controls to set an unexamined client in a selected state in a default state.

If the operator selects one client from the list shown in FIG. 5 using the selection unit 17 and presses the examination start button 21 (YES in step S13), a radiographing list that indicates the contents of the examination information and radiographing information of the selected client (FIGS. 3 and 4) is displayed.

If a radiographing process to be executed is selected from the radiographing information list shown in FIG. 4 in step S14, a radiographic apparatus to be used in that radiographing process is determined in step S15.

In this embodiment, assume that a radiographic apparatus that actually performs a radiographing operation is not designated upon placing an order at the ordering apparatus. This is to change a radiographic apparatus to be used depending on radiographic apparatuses connected to the X-ray examination progress apparatus 1. Therefore, the X-ray examination progress apparatus 1 determines a radiographing process to be done and an apparatus to be used for that process in step S15.

In this embodiment, a radiographic apparatus to be used is assigned to a radiographing method ID and radiographing direction, which are given to a radiographing method name in one-to-one correspondence therebetween, and a table having this information is held in the management unit 12 of the X-ray examination progress apparatus 1. FIG. 6 shows an example of this table. The X-ray examination progress apparatus 1 determines a radiographic apparatus to be used for radiographing on the basis of the radiographing method ID and radiographing direction contained in the radiographing information using this table. Note that the contents of the table shown in FIG. 6 can be changed via the change unit 16 in FIG. 1A. Hence, assignment of radiographic apparatuses determined based on the radiographing method ID and radiographing direction can be changed in correspondence with a change in radiographic apparatus connected to the X-ray examination progress apparatus 1, operator's needs, or the like.

For example, when two radiographing processes, i.e., "radiographing operation 1" that instructs "chest front" radiographing operation and "radiographing operation 2" that instructs "chest side" radiographing operation are displayed in the radiographing operation list, as shown in FIG. 4, upon depression of the examination start button 21 in FIG. 5, "chest front" is automatically set in a selected state (step S14). Since chest front radiographing operation of "radiographing operation 1" has a radiographing method ID=1000 and a radiographing direction=PA, the X-ray examination progress apparatus 1 determines the FPD 3 as the radiographic apparatus to be used from the table shown in FIG. 6 (step S15).

Since this radiographing operation is the first one by the FPD 3 in the present examination order (YES in step S16), the examination information shown in FIG. 3 is transferred to the examination order information reception unit 302 of the FPD 3 via the examination order information transmission unit 13 of the X-ray examination progress apparatus 1 in step S17. On the other hand, if the radiographing operation to be done by that radiographic apparatus in that examination order is the second or subsequent one (NO in step S16), since the radiographic apparatus already has the examination information, the flow jumps to step S18.

In step S18, the radiographing information of the selected radiographing process ("radiographing operation 1" in FIG. 4 in this case) is transferred to the examination order information reception unit of the selected radiographic apparatus (FPD 3 in this case) via the examination order information transmission unit 13 of the X-ray examination progress apparatus 1.

Upon receiving execution information based on the sent radiographing information from the radiographic apparatus (FPD 3 in this case) via the examination order execution information reception unit 14 (step S19), it is checked in step S20 if all radiographing processes of the client selected in step S13 are complete. If NO in step S20, the flow returns to step S14; otherwise, the flow advances to step S21. It is checked in step S21 if radiographing processes of all clients on the examination order information list are complete. If NO in step S21, the flow returns to step S13; otherwise, the flow returns to step S11 to wait for reception of the next examination order information.

The FPD 3 uniquely determines a parameter set (radiographing parameter set) used in radiographing on the basis of parameters in the examination information sent in step S17 (FIG. 2) and the radiographing information sent in step S18. The parameter set setup process will be described in detail below with reference to the flow chart of FIG. 7 and tables of FIGS. 8 to 12. Note that the radiographing parameter set is set up with reference to the input examination information and radiographing information, a basic parameter set stored in the parameter set storage unit 305, and system setup values stored in the system default value storage unit 306. In this case, radiographing processes using the FPD 3 will be explained below. When radiographing processes are made using the CR 2, a radiographing parameter set is setup using the same arrangement in the CR 2.

Upon receiving the examination information and radiographing information from the X-ray examination progress apparatus 1, the setup processing unit 308 looks up the examination information shown in FIG. 3 and the contents of "radiographing operation 1" in FIG. 4 as an order parameter shown in FIG. 8 (step S31). A basic parameter set is uniquely determined based on the radiographing method ID and radiographing direction of these contents of the order parameter information, and is read out from the parameter set storage unit (step S32). FIG. 9 shows an example of a basic parameter set selected in this way, and this parameter set is temporarily stored as "a radiographing parameter set" shown in FIG. 8. Note that (N/A) is set in the columns of parameters of items which are not handled in FIGS. 8 and 9. Also, FIG. 9 shows an example of system setup parameters, which are independent of the parameter set shown in FIG. 9, together.

In the processes in step S33 and subsequent steps, parameters of respective items of the radiographing parameter set are adjusted. It is checked if each of respective parameters of the radiographing parameter set shown in FIG. 8 is designated in the received order parameter information (step S33).

For example, an X-ray aperture value is a parameter required for an radiographing operation to control the X-ray aperture value before performing a radiographing operation, and in the example shown in FIG. 8, X-ray aperture value information is contained as 35 cm×35 cm in the order parameter information (YES in step S33). In this case, the flow advances to step S34 to check if an instruction for changing a process using another parameter is detected, i.e., if "*" indicating a change instruction is appended to an order parameter (step S34). If "*" is appended (YES in step S34), a change process can be done within the radiographic apparatus on the basis of predetermined rules. Therefore, a change process is done on the basis of the above-mentioned rules in step S35. FIG. 10 shows an example of such rules. A value determined based on the rules is used as a radiographing parameter in place of a basic parameter. In this example, since the age of a patient (person to be examined) is 15 years old or more, parameter (35 cm×35 cm) designated in the order parameter information, as shown in FIG. 8, is used. However, if the age of a patient is less than 15 years old, an aperture value obtained by 20% reducing 35 cm×35 cm is used. In this example, a parameter for controlling the X-ray aperture value is determined based on the age of a patient. Also, a parameter used to make at least one of X-ray aperture value control, relative position control between the X-ray tube and the image sensor, output format control, radiographed image extraction (trimming) control, X-ray generation condition control, and the like can be determined before radiographing operation in accordance with the received patient information such as a patient's name, ID information, height, weight, gender, and the like.

If no "*" is appended in step S34, i.e., if no change process is required (NO in step S34), a parameter designated in the order parameter information replaces a basic parameter (step S36). In this case, a parameter which does not require any change process is a height offset value of radiographing information, and a basic parameter (0 mm) is replaced by a value (20 mm) in the order parameter. The relative height between the X-ray tube and the sensor is controlled before radiographing operation is performed in accordance with this height offset value. Note that the height offset value is given as an offset value of the central position of an X-ray stop aperture portion with respect to that of an image sensor effective region. Alternatively, an offset value in a width direction perpendicular to the height may be used, or two-dimensional offset values in both the height and width directions may be used.

If the order parameter information does not include any parameter like DICOM tag data description information (NO in step S33), it is confirmed if information indicated by a basic parameter is a system lookup instruction (step S37). If YES in step S37, the system setup values shown in FIG. 9 are looked up. In the example shown in FIG. 8, since the DICOM tag data description information item of a basic parameter is a system lookup instruction (YES in step S37), a system setup value (0010, 1000)=B shown in FIG. 9 is used and a process for setting a value "B" in an area (0010, 1000) of a DICOM header is enabled (step S38).

If a parameter is not included in the order parameter information (NO in step S33), and a system lookup instruction is not set (NO in step S37), it is confirmed in step S39 if an instruction for setting a parameter by another method is set as a basic parameter. If no such instruction is set, a value pre-set in the basic parameter set is used in step S41. Such parameters include a tube current in the example in FIG. 8, and 100 mA as a value of the parameter set is used as a tube current.

On the other hand, if an instruction for setting a parameter by another method is set, a parameter is changed by the corresponding method (step S40) and is set. Such items include horizontal reverse of an image and an exposure time in the example shown in FIG. 8. Horizontal reverse of an image sets if an image is rotated or reversed in a direction designated in advance in accordance with a radiographing direction. In this case, the basic parameter set includes an image horizontal reverse parameter "follow chest table". In this case, since a chest front PA radiographing operation is to be made, FIG. 11 shows an example of the chest table in such case. This chest table is set in advance, and horizontal reverse is determined based on this table. Note that similar tables are set and held for respective portions to be radiographed.

On the other hand, the order parameter information (an exposure time) includes no exposure time value, and "use statistical information" is set in the basic parameter set. In this scheme, the parameter is uniquely determined in correspondence with the radiographing method ID and radiographing direction, and a setup condition (parameter) is determined in advance by exploiting a statistical value of actual exposure execution times of previous radiographing processes. If radiographing is done, the X-ray generation apparatus 5 sends an actual exposure condition. This condition is stored in the management unit 301. A time obtained by calculating one of indices such as an average value, median value, and mode of radiographing execution times (actual exposure times) for a predetermined number of times of previous radiographing processes, e.g., 10 radiographing processes is used. In this method, since a radiographing condition in correspondence with a pair of radiographing method ID and radiographing direction does not largely vary, it is designated based on previous records in place of being input from the X-ray examination progress apparatus 1 in advance. The radiographing execution time is received from the X-ray generation apparatus 5 directly or via an external X-ray examination apparatus after the radiographing operation. In this case, if a reception unit for that purpose is not available, the radiographing execution time may be determined based on the output from an X-ray monitor that measures the irradiation time of X-rays. Thus obtained exposure time is used as a predicted radiographing execution time to determine the grid moving speed in accordance with this time information. Using an optimal moving speed, interference fringes (a stripe pattern due to the grid) can be prevented.

Figure 7:
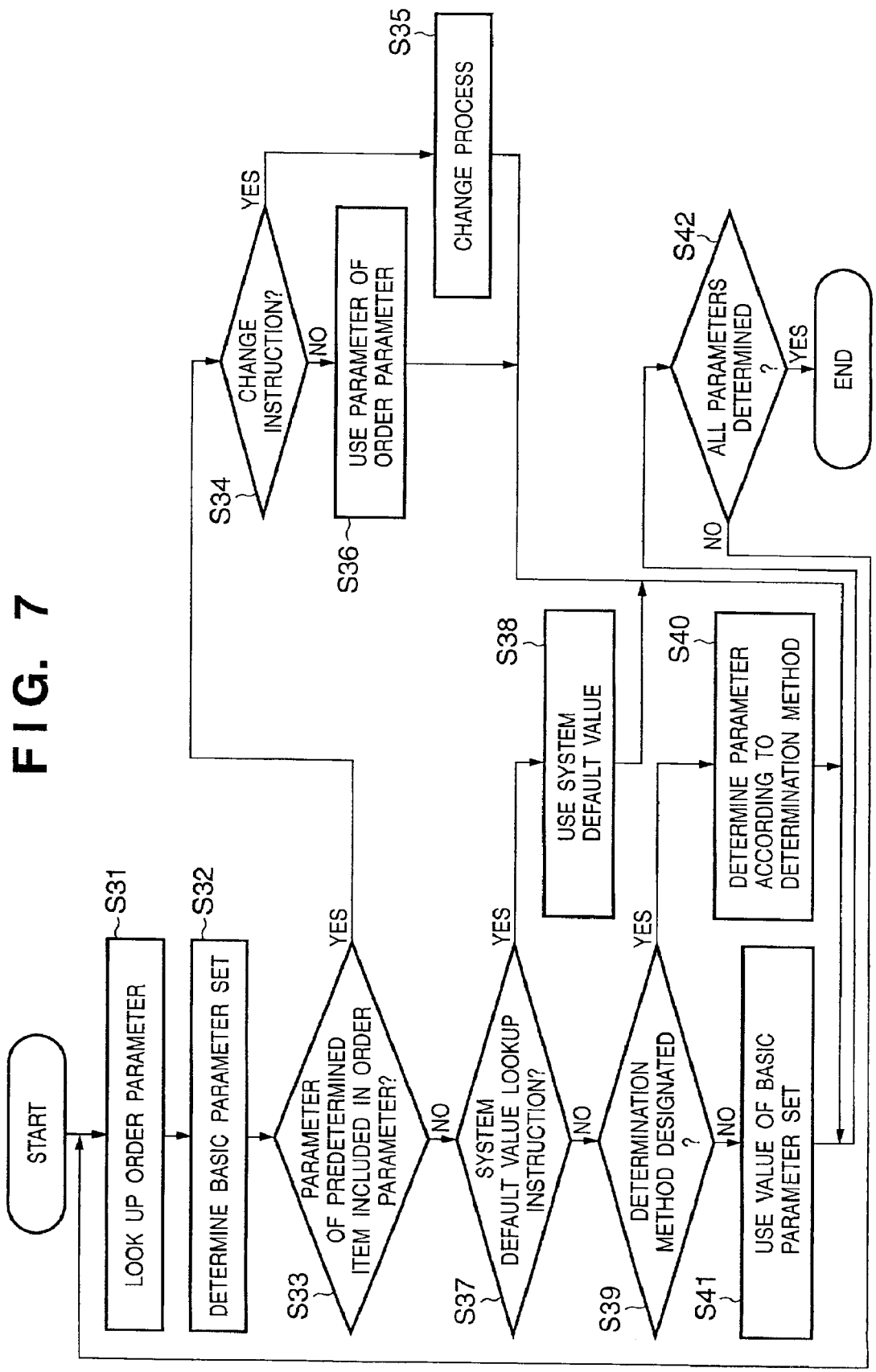
FIG. 7 is a flow chart showing a parameter setup sequence according to the embodiment of the present invention.

The final control parameters are determined according to the process shown in the flow chart of FIG. 7, as described above, and such items for which parameters are to be determined also include the following items.

Output Format Information

This information is used to extract (trim) a radiographed image. For example, in case of large square designation, a 35 cm×35 cm image area is extracted as an image, which is converted into digital image data to be output. In case of 35 cm×43 cm, an image area corresponding to that size is extracted as an image, which is converted into digital image data to be output.

Character Size, Position

This information indicates the size and position of a character to be inserted on a radiographed image. Note that insertion of characters indicates not only a case wherein characters are rendered as image data in an image, but also a case wherein characters are superimposed on an image upon displaying an image on a CRT or the like. In the example shown in FIG. 8, an instruction is set as an order parameter, and is valid. However, if no instruction is set as an order parameter, and an instruction "use system value" is set in a parameter set, the character size and position are set together in accordance with those determined in advance for each radiographing operation, as shown in FIG. 12. As for image horizontal reverse, a parameter set is available in the above example, and is valid. If a parameter set includes an instruction "use system value", a parameter that concerns horizontal reverse is set in accordance with system information, as shown in FIG. 12, for example.

Transfer Destination of Image

A transfer destination set in an order parameter or basic parameter is designated before the beginning of a radiographing operation. The transfer destination can be changed in accordance with an instruction from the transfer destination setup information reception unit 19. With this instruction, the transfer destinations of all images, radiographing operations of which are underway, can be changed at the same time, and those of radiographed and non-transferred images can also be changed. In this manner, if a trouble has occurred in a printer set before the beginning of a radiographing operation, switching to an alternative printer can be instructed from the X-ray examination progress apparatus 1.

Density Setup of Generation Apparatus.

Density setup information of a generation apparatus is output from the X-ray generation apparatus communication units 207 and 307 to the X-ray generation apparatuses 4 and 5. In the FPD 3, the density setup information is used to control the X-ray intensity. An AEC (Auto Exposure Control) unit of the X-ray generation apparatus 5 monitors the X-ray dose of exposure and controls to close exposure at a predetermined threshold dose, and the density setup information is used to increase/decrease the film density in conventional analog radiographing. However, in the FPD 3, even when the X-ray intensity is controlled, a predetermined image density is maintained by an automatic mechanism of an image processing, and a result which is discordant with the intention of the user who used an analog system is obtained. For this reason, in the system setup, a parameter setup for grayscale processing of a radiograph is appropriately changed on the basis of a density setup value so as to attain an image processing as if the density changed in correspondence with the setup value.

Figure 13:
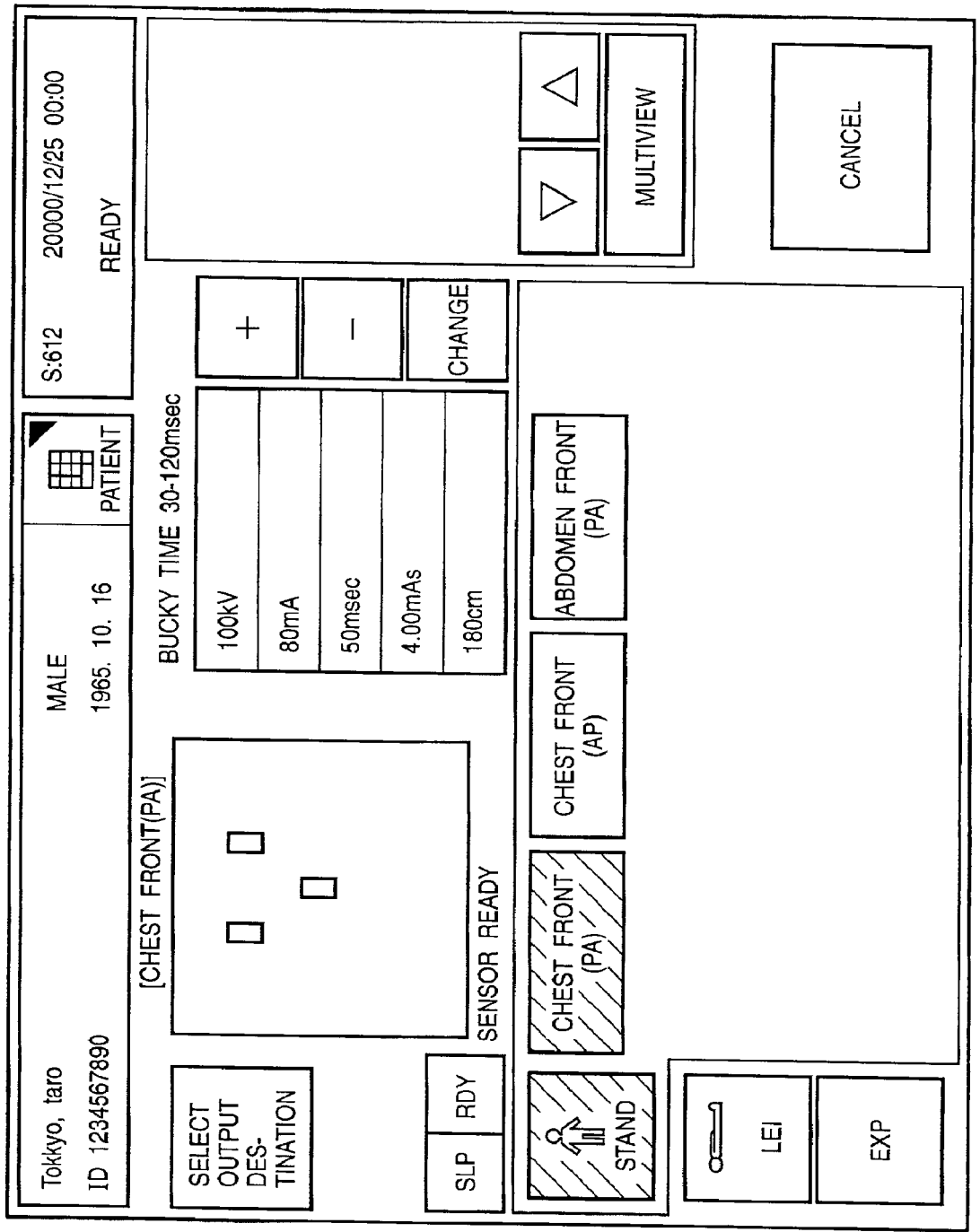
FIG. 13 shows an example of a chest front radiographing guide window according to the embodiment of the present invention.
Figure 14A:
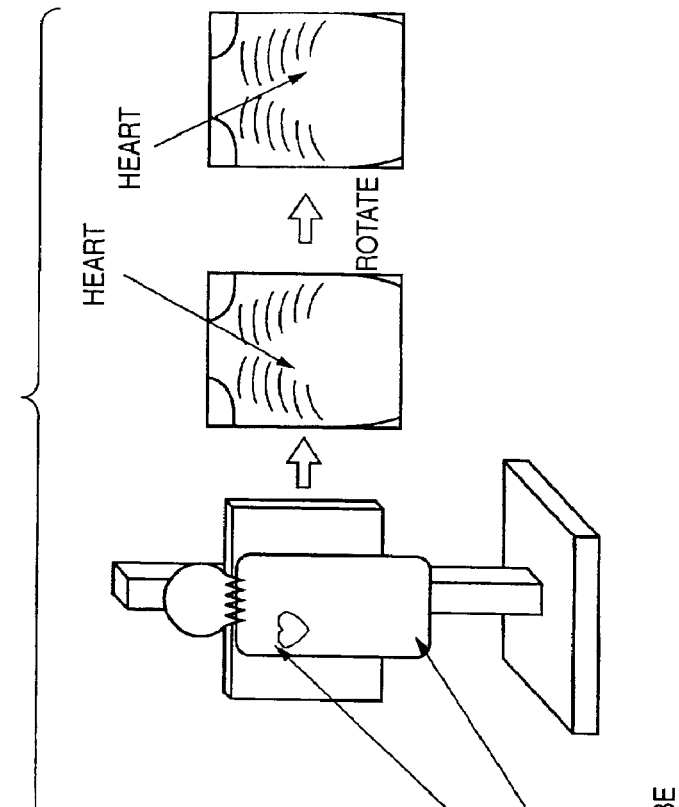
FIGS. 14A and 14B are views for explaining conventional chest radiographing examples.
Figure 14B:
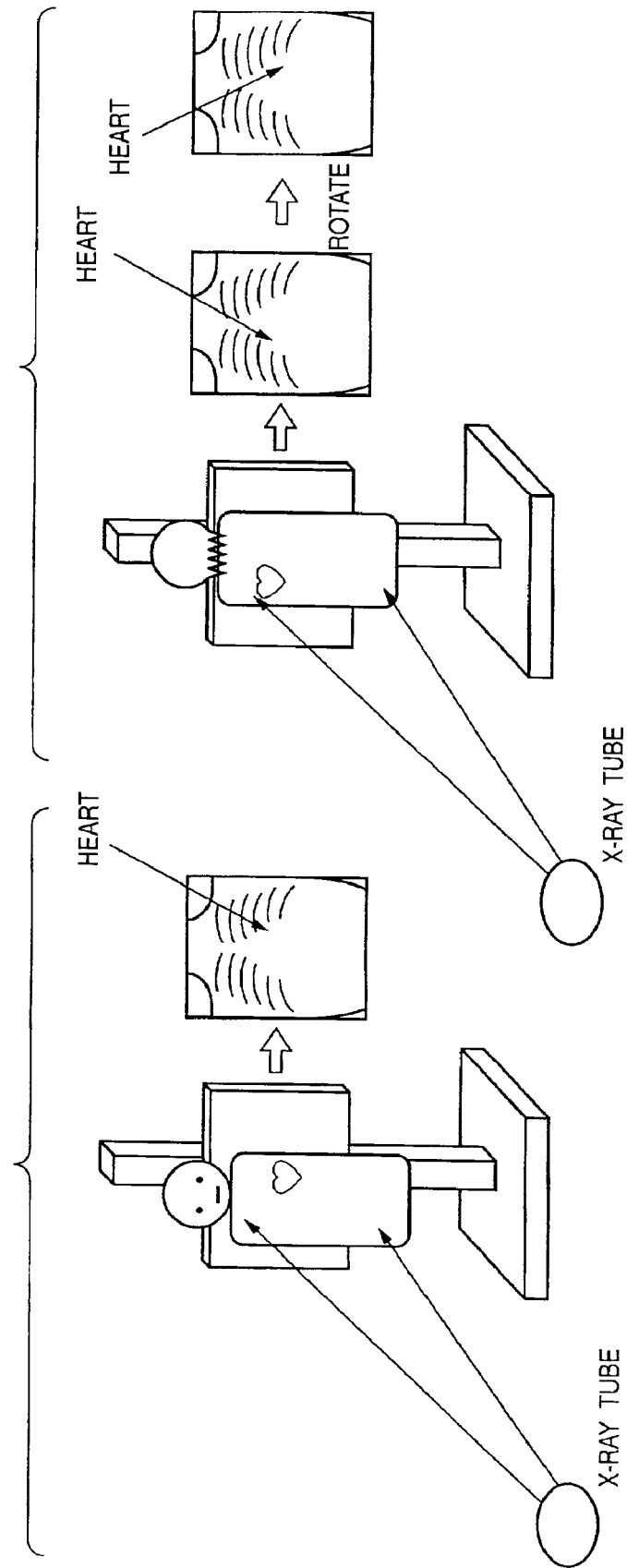
Figure 15A:
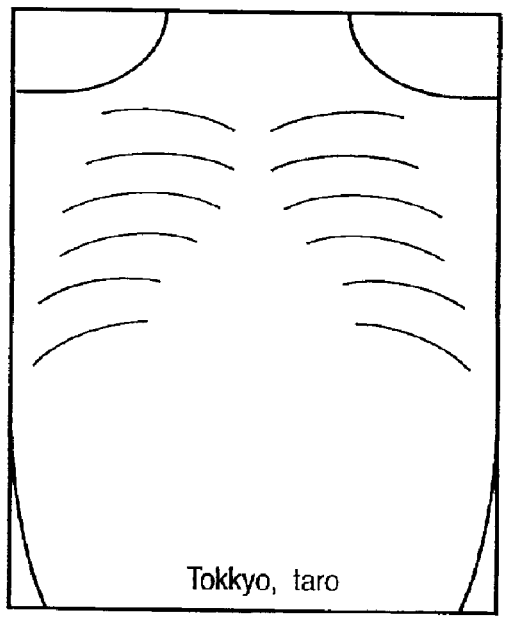
FIGS. 15A and 15B are views showing a prior art in which the patient's name is superimposed on a radiograph.
Figure 15B:
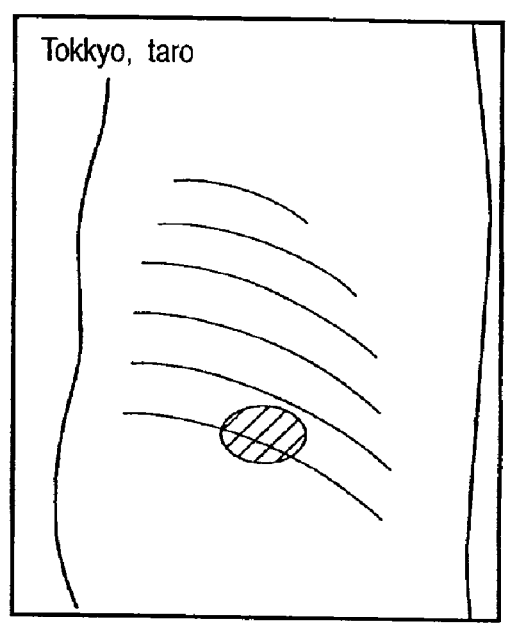

In this manner, the radiographing condition of the FPD 3 is set in accordance with the radiographing information, a window shown in FIG. 13 is displayed on the console 312 of the FPD 3, and a "chest front (PA)" radiographing button is automatically selected, thus completing preparation for a radiographing operation.

Likewise, when a radiographing process of "radiographing operation 2" in FIG. 4 is to be made, since a radiographing process using the FPD 3 is determined based on the default table shown in FIG. 6, radiographing parameters are set in the FPD 3 in the same sequence or manner as in the above description.

When the radiographing processes in both the FPD 3 and CR 2 are complete, and the X-ray examination progress apparatus 1 outputs an examination end instruction, both the FPD 3 and CR 2 begin to output images from the image transfer units 211 and 311 toward the designated transfer destinations using a DICOM protocol.

In the processing sequence shown in FIG. 7, a basic parameter set is read out on the basis of the radiographing method ID and radiographing direction, and the readout parameter set is then changed. However, the processing sequence of the present invention is not limited to such specific one, and parameters need only be set based on the order parameters in preference to the basic parameter set. For example, it may be confirmed for each item if an order parameter has a setup value, and if a setup value is available, it is made valid, and if no setup value is available, a parameter of a corresponding item may be read out from the basic parameter set which is uniquely determined based on the radiographing method ID and radiographing direction.

A radiographing instruction from the X-ray examination progress apparatus 1 is sent to the radiographic apparatus 2 or 3, and the radiographing execution result is returned to the X-ray examination progress apparatus 1. In order to obviate the need for changing the return destination of such radiographing execution result information from another apparatus to the X-ray examination progress apparatus 1, the ID value of the X-ray examination progress apparatus 1 is given in advance as the return destination of the radiographing execution result information upon sending radiographing order information to return the radiographing execution result information to the apparatus 1.

In the above description, the X-ray examination progress apparatus 1 controls two radiographic apparatuses to make radiographing operations for an examination for the sake of simplicity. However, in practice, the X-ray examination progress apparatus is often controllably connected to up to 10 radiographic apparatuses, and is constructed so that a GUI window for controlling progress of examination is displayed on each of a plurality of portable terminals via wireless channels, and selection, instruction, and the like concerning the examination progress can be made using a touch panel on each portable terminal. By connecting the portable terminals and the X-ray examination progress apparatus via a wireless communication system (a wireless communication unit 26 of the X-ray examination progress apparatus 1, and wireless communication units 20 and 23 connected to external change units 21 and 24, and selection units 22 and 25) that exploits a Web server-client technique, the operator can easily remote-control the X-ray examination progress apparatus from his or her portable terminal without going to a place where the X-ray examination progress apparatus is actually equipped, thus radiographing being executed efficiently using one or a plurality of radiographic apparatuses.

In the above embodiment, the radiographing parameter set is determined by the radiographic apparatus. Alternatively, the radiographing parameter set may be determined by the X-ray examination progress apparatus, and the determined radiographing parameter set may be sent to the radiographic apparatus.

More specifically, the parameter set storage unit 205 or 305, the system default value storage unit 206 or 306 and setup processing unit 208 or 308 in the radiographic apparatus 2 or 3 shown in FIGS. 1A to 1C may be arranged in the X-ray examination progress apparatus 1, and may be connected to the management unit 12. In this case, the X-ray examination progress apparatus sets the parameters, and sends the set parameters instead of the examination order to an appropriate radiographic apparatus.

<Other Embodiment>

Note that the present invention may be applied to either a system constituted by a plurality of apparatuses (e.g., an X-ray examination progress apparatus, interfaces, radiographic apparatuses, X-ray generation apparatuses, and the like) or an arrangement that integrates an X-ray examination progress apparatus and a radiographic apparatus.

Further, the object of the present invention can also be achieved by providing a storage medium storing program codes for performing the aforesaid processes to a computer system or apparatus (e.g., a personal computer), reading the program codes, by a CPU or MPU of the computer system or apparatus, from the storage medium, then executing the program.

In this case, the program codes read from the storage medium realize the functions according to the embodiment, and the storage medium storing the program codes constitutes the invention.

Further, the storage medium, such as a floppy disk, a hard disk, an optical disk, a magneto-optical disk, CD-ROM, CD-R, a magnetic tape, a non-volatile type memory card, and ROM can be used for providing the program codes.

Furthermore, besides aforesaid functions according to the above embodiment are realized by executing the program codes which are read by a computer, the present invention includes a case where an OS (operating system) or the like working on the computer performs a part or entire processes in accordance with designations of the program codes and realizes functions according to the above embodiment.

Furthermore, the present invention also includes a case where, after the program codes read from the storage medium are written in a function expansion card which is inserted into the computer or in a memory provided in a function expansion unit which is connected to the computer, CPU or the like contained in the function expansion card or unit performs a part or entire process in accordance with designations of the program codes and realizes functions of the above embodiment.

In a case where the present invention is applied to the aforesaid storage medium, the storage medium stores program codes corresponding to the flowchart shown in FIG. 7 described in the embodiment.

The present invention is not limited to the above embodiments and various changes and modifications can be made within the spirit and scope of the present invention. Therefore to apprise the public of the scope of the present invention, the following claims are made.

What is claimed is:

1. A radiographic apparatus which performs radiography using examination request information received from an external apparatus, wherein the examination request information includes at least information on a portion to be radiographed of a human body, a parameter set and priority information for a parameter, comprising:

an X-ray generation unit which generates X-rays;

a storage unit adapted to store default radiographing parameter sets for a plurality of portions to be radiographed of a human body;

a condition determination unit adapted to determine a radiation condition of said X-ray generation unit on the basis of the parameter set in the received examination request information and one of the default radiographing parameter sets, stored in said storage unit, corresponding to the portion to be radiographed; and a control unit adapted to control said X-ray generation unit on the basis of the determined radiation condition, wherein if a value of a parameter in the parameter set in the received examination request information is different from a value of a corresponding parameter in the default radiographing parameter set, said condition determination unit selects a value of the parameter on the basis of the priority information.

2. The apparatus according to claim 1, further comprising:

a reception unit adapted to receive transfer destination information from the external apparatus wherein said condition determination unit determines a parameter indicating a transfer destination of a radiographed image on the basis of the received transfer destination information, and said control unit controls said transfer destination setup unit in accordance with the determined parameter.

3. The apparatus according to claim 1, further comprising a stop for limiting an X-ray irradiation aperture, wherein said condition determination unit determines a parameter for limiting the X-ray irradiation aperture by said stop on the basis of one of the default parameter sets corresponding to the portion to be radiographed of a human body and the parameter set in the received examination request information, and said control unit controls said stop in accordance with the determined parameter.

4. The apparatus according to claim 1, further comprising an X-ray sensor which converts the X-ray radiation to image data, wherein said condition determination unit determines as the radiation condition, a parameter associated with a relative position relation between said X-ray generation unit and an X-ray sensor, and said control unit controls said X-ray generation unit in accordance with the determined parameter.

5. The apparatus according to claim 1, further comprising:

an X-ray sensor which converts the X-ray radiation to image data; and an image processing unit adapted to perform image processes on the image data, wherein said condition determination unit determines a parameter indicating an output format on the basis of one of the default parameter sets corresponding to the position to be radiographed of a human body and the parameter set in the received examination request information, and said control unit controls said image processing unit to extract at least a part of the image data in accordance with the determined parameter.

6. The apparatus according to claim 1, further comprising:
an X-ray sensor which converts the X-ray radiation to image data; and
an image processing unit adapted to perform image processes on the image data,
wherein said condition determination unit determines a parameter for either rotation or reverse of the image data on the basis of one of the default parameter sets corresponding to the position to be radiographed of a human body and the parameter set in the received examination request information, and said control unit controls said image processing unit in accordance with the determined parameter.

7. The apparatus according to claim 1, wherein said condition determination unit determines as the radiation condition a parameter indicating density on the basis of one of the default parameter sets corresponding to the position to be radiographed of a human body and the parameter set in the received examination request information, and said control unit controls an X-ray generation amount of said X-ray generation unit in accordance with the determined parameter.

8. The apparatus according to claim 6, further comprising an image processing unit adapted to perform image processes on a radiographed image,
wherein said image processing unit performs the image processes to increase a density of the radiographed image if the determined parameter designates a large density value, and to decrease a density of the radiographed image if the determined parameter designates a small density value.

9. The apparatus according to claim 1, further comprising:
an X-ray sensor which converts the X-ray radiation to image data; and
an image processing unit adapted to perform image processes on the image data,
wherein said condition determination unit determines characters to be inserted on the image data, and said control unit controls said image processing unit to insert the characters.

10. The apparatus according to claim 9, wherein said condition determination unit determines the characters in accordance with at least one of information of a portion to be radiographed, radiographing direction, and right/left distinction of a portion to be radiographed.

11. The radiographic apparatus according to claim 9, wherein said condition determination unit determines parameters for a size and position of the characters to be inserted on the image data on the basis of one of the default parameter sets corresponding to the portion to be radiographed of a human body and the parameter set in the received examination request information, and said control unit controls said image processing unit in accordance with the determined parameters.

12. The apparatus according to claim 1, wherein the radiation condition contains X-ray exposure time, and
said apparatus further comprises an arrangement for determining a grid moving speed in accordance with the determined X-ray exposure time information.

13. The apparatus according to claim 12, wherein the determined X-ray exposure time is a time calculated based on a statistic of actual X-ray exposure times for previous radiographing operations made based on a predetermined radiation condition determined by said condition determination unit.

14. The apparatus according to claim 13, wherein the statistic is one of an average value, median value, and mode.

15. The apparatus according to claim 13, wherein the actual X-ray exposure time is received from an external X-ray examination apparatus or X-ray generation apparatus.

16. The apparatus according to claim 13, further comprising an X-ray monitor for detecting X-ray irradiation, wherein the actual X-ray exposure time is determined based on an output from said X-ray monitor.

17. The apparatus according to claim 1, wherein said storage unit stores second default radiographing parameter sets, and
wherein when one of the default radiographing parameter sets has an instruction to use a second default parameter set, said condition determination unit sets the second default parameter set as the radiation condition corresponding to the instruction.

18. The apparatus according to claim 1, wherein said storage unit stores second default radiographing parameter sets, and
wherein when one of the default radiographing parameter sets has an instruction to use second default parameter sets, said condition determination unit sets the second default parameter sets as the radiation condition corresponding to the instruction.

19. The radiographic apparatus according to claim 1, wherein if there is a parameter which is not defined in the default parameter set and the parameter set in the received examination request information, said condition determination unit uses a system setting parameter in the external apparatus as the undefined parameter.

20. The radiographic apparatus according to claim 1, wherein the information on a portion to be radiographed of a human body includes at least a portion of a human body or a radiographing direction.

21. The radiographic apparatus according to claim 1, wherein the parameter set in the received examination request information includes at least one of tube voltage, tube current, and irradiation time of said X-ray generation unit.

22. A control apparatus which is connectable to a plurality of types of radiographic apparatuses, each comprising an X-ray generation unit which generates X-rays and an X-ray sensor which converts the X-ray radiation image data, and outputs information to the radiographic apparatuses on the basis of examination request information received from an external apparatus, comprising:
an apparatus selection unit which selects a radiographic apparatus from the plurality of types of radiographic apparatuses to be used on the basis of the received examination request information; and
a communication unit adapted to send information that pertains to the examination request information to the selected radiographic apparatus.

23. The apparatus according to claim 22, wherein the apparatus is communicatable with a plurality of input/output apparatuses, wherein processes based on inputs from said plurality of input/output apparatuses can be executed in parallel to each other.

24. The apparatus according to claim 23, wherein said communication unit includes a wireless communication unit, and is communicatable with said plurality of input/output apparatuses via wireless channels.

25. The apparatus according to claim 22, further comprising a setting unit for setting a transmission destination of an X-ray image obtained by a radiographic apparatus.

26. The apparatus according to claim 22, wherein the examination request information contains at least information on an object to be radiographed of a human body, a parameter set, and priority information for a parameter.

27. The apparatus according to claim 22, further comprising a setting unit for setting a radiation condition of said X-ray generation unit of the selected radiographic apparatus on the basis of the received examination request information.

28. A control apparatus which is connectable to a radiographic apparatus comprising an X-ray generation unit which generates X-rays and an X-ray sensor which converts the X-ray radiation to image data, and outputs information to the radiographic apparatus on the basis of examination request information received from an external apparatus, wherein the examination request information includes at least information on a portion to be radiographed of a human body, a parameter set, and a priority information for a parameter, comprising:
 a storage unit adapted to store default radiographing parameter sets for a plurality of portions to be radiographed of a human body;
 a condition determination unit adapted to determine a radiation condition of said X-ray generation unit on the basis of the parameter set in the received examination request information and one of the default radiographing parameter sets, stored in said storage unit corresponding to the portion to be radiographed; and
 a communication unit adapted to send the determined radiation condition to the radiographic apparatus,
 wherein if a value of a parameter in the parameter set in the received examination request information is different from a value of a corresponding parameter in the default radiographing parameter set, said condition determination unit selects a value of the parameter on the basis of the priority information.

29. The apparatus according to claim 28, wherein the apparatus is connectable to a plurality of radiographic apparatuses, and further comprising an apparatus selection unit which selects a radiographic apparatus out of the plurality of radiographic apparatuses to be used on the basis of the received examination request information.

30. The apparatus according to claim 28, wherein the apparatus is communicatable with a plurality of input/output apparatuses, wherein processes based on inputs from said plurality of input/output apparatuses can be executed parallel to each other.

31. The apparatus according to claim 30, wherein said communication unit includes a wireless communication unit, and is communicatable with said plurality of input/output apparatuses via wireless channels.

32. The apparatus according to claim 28, further comprising a setting unit for setting a transmission destination of an X-ray image obtained by a radiographic apparatus.

33. A radiographing method of performing radiography using examination request information received from an external apparatus, wherein the examination request information includes at least information on a portion to be radiographed of a human body, a parameter set, and priority information for a parameter, comprising:
 selecting one of default radiographing parameter sets for a plurality of portions to be radiographed of a human body from a storage unit, the selected default parameter set corresponding to the received portion to be radiographed;
 determining a radiation condition of a X-ray generation unit which generates X-rays on the basis of the parameter set in the received examination request information and the selected default radiographing parameter set; and
 controlling the X-ray generation unit on the basis of the determined radiation condition,
 wherein if a value of a parameter in the parameter set in the received examination request information is different from a value of a corresponding parameter in the default radiographing parameter set, said condition determination unit selects a value of the parameter on the basis of the priority information.

34. A control method of controlling a plurality of radiographic apparatuses, each comprising an X-ray generation unit which generates X-rays and an X-ray sensor which converts the X-ray radiation to image data on the basis of examination request information received from an external apparatus, comprising:
 selecting a radiographic apparatus out of the plurality of radiographic apparatuses to be used on the basis of the received examination request information; and
 sending information that pertains to the examination request information to the selected radiographic apparatus.

35. A control method of controlling a plurality of radiographic apparatuses, each comprising an X-ray generation unit which generates X-rays and an X-ray sensor which converts the X-ray radiation to image data on the basis of examination request information received from an external apparatus, wherein the examination request information includes at least information on a portion to be radiographed of a human body, a parameter set, and priority information for a parameter, comprising:
 selecting one of default radiographing parameter sets for a plurality of portions to be radiographed of a human body from a storage unit, the select default parameter set corresponding to the received portion to be radiographed:
 determining a radiation condition of the X-ray generation unit on the basis of the parameter set in the received examination request information and the selected default radiographing parameter set; and
 sending the determined radiation condition to the radiographic apparatus,
 wherein if a value of a parameter in the parameter set in the received examination request information set is different from a value of a corresponding parameter in the default radiographing parameter set, said condition determination unit selects a value of the parameter on the basis of the priority information.

36. A computer program product comprising a computer usable medium having computer readable program code means embodied in said medium for realizing a radiographing method described in claim 33.

37. A computer program product comprising a computer usable medium having computer readable program code means embodied in said medium for realizing a control method described in claim 34.

38. A computer program product comprising a computer usable medium having computer readable program code means embodied in said medium for realizing a control method described in claim 35.

* * * * *

UNITED STATES PATENT AND TRADEMARK OFFICE
CERTIFICATE OF CORRECTION

PATENT NO. : 6,859,513 B2
DATED : February 22, 2005
INVENTOR(S) : Tsukasa Sako

It is certified that error appears in the above-identified patent and that said Letters Patent is hereby corrected as shown below:

<u>Title page,</u>
Item [57], ABSTRACT,
Line 3, "externa ol" should read -- external --.

<u>Column 5,</u>
Line 58, "metod" should read -- method --.

<u>Column 14,</u>
Line 28, "apparatus" should read -- apparatus, --.

Signed and Sealed this

Twenty-fourth Day of January, 2006

JON W. DUDAS
*Director of the United States Patent and Trademark Office*